United States Patent [19]

Kniebes

[11] Patent Number: 5,100,244
[45] Date of Patent: Mar. 31, 1992

[54] GAS CALORIMETER AND METHOD OF MEASURING THE CALORIFIC VALUE OF FUEL GASES

[75] Inventor: Duane V. Kniebes, Boulder, Colo.

[73] Assignee: Precision Measurement, Inc., Duncanville, Tex.

[21] Appl. No.: 564,699

[22] Filed: Aug. 7, 1990

Related U.S. Application Data

[63] Continuation-in-part of Ser. No. 348,146, May 2, 1989, abandoned, which is a continuation of Ser. No. 37,024, Apr. 10, 1987, abandoned.

[51] Int. Cl.[5] ............................................. G01N 25/30
[52] U.S. Cl. .......................................... 374/36; 374/37
[58] Field of Search ............................. 374/36, 37, 38

[56] References Cited

U.S. PATENT DOCUMENTS

| | | | |
|---|---|---|---|
| 2,825,226 | 3/1958 | Daley et al. | 374/36 |
| 3,072,468 | 1/1963 | Stitzer | 374/37 |
| 3,777,562 | 12/1973 | Clingman | 374/37 |
| 4,306,451 | 12/1981 | Szonntagh | 374/36 |
| 4,337,654 | 7/1982 | Austin et al. | 374/37 |
| 4,433,922 | 2/1984 | Bohl et al. | 374/36 |
| 4,614,721 | 9/1986 | Goldberg | 374/37 |

FOREIGN PATENT DOCUMENTS

| | | | |
|---|---|---|---|
| 1123955 | 10/1956 | France | 374/36 |

Primary Examiner—Allan N. Shoap
Assistant Examiner—Diego F. F. Gutierrez
Attorney, Agent, or Firm—Johnson & Gibbs

[57] ABSTRACT

A gas calorimeter and method of measuring the calorific value of fuel gases in which a fixed volume of gas to be measured is burned in a controlled environment. The temperature increase of the air in the environment caused by the burning is used to determine the calorific value of the gas. The gas to be measured is intermittently supplied to the controlled environment using a base plate which has portions defining a plurality of dispersion holes in a distributed manner so that a greater number of the plurality of dispersion holes are in and around the periphery of the base plate than are in and toward the center of the base plate.

20 Claims, 2 Drawing Sheets

5,100,244

GAS CALORIMETER AND METHOD OF MEASURING THE CALORIFIC VALUE OF FUEL GASES

This is a continuation-in-part of application Ser. No. 07/348,146, filed May 2, 1989, now abandoned, which is a continuation, of application Ser. No. 07/037,024, filed Apr. 10, 1987 now abandoned.

BACKGROUND OF THE INVENTION

This invention relates to a gas calorimeter and method, and, more specifically, to a device and method for measuring the calorific value of fuel gases.

Calorimeters are widely utilized for determining the calorific value (heat content) of fuel gases, especially gases that are sold in commerce according to their heat content, often expressed in British thermal units per standard cubic foot of volume. Most gas calorimeters in current use employ continuously burning flames which are supplied with gas and air by metering devices that measure the flow rates of the gas and air to a burner. Various techniques are utilized to obtain a precise measurement for the calorific value of the gas in these systems. For example, some techniques utilize direct measurement of the temperature of the flame or of a fluid, such as air or water, after the heat from the flame is transferred to the fluid. However, most of these techniques require a continuous flow of the gas to be tested which requires a relatively large volume of gas. Also, the temperatures required in these known techniques have to be relatively high and have to be maintained over a relatively long period of time, which causes severe heat losses. As a result, expensive gas and air metering components and environmental control systems are required. Further, the known systems are relatively complex and bulky and are unsuitable for remote field locations.

SUMMARY OF THE INVENTION

It is therefore an object of the present invention to provide a gas calorimeter and method which provides an accurate measurement of the calorific value, including gross calorific value, of fuel gases.

It is a further object of the present invention to provide a calorimeter and method of the above type which utilizes a noncontinuous, pulse-type measurement and thus requires a relatively small volume of sample gas.

It is still a further object of the present invention to provide a calorimeter and method of the above type in which the temperature of air surrounding the gas does not have to be maintained at high levels over long periods of time and which thus minimizes heat losses.

It is a further object of the present invention to provide a calorimeter and method of the above type in which the necessity of relatively expensive metering components and environmental control systems are eliminated.

It is a further object of the present invention to provide a calorimeter of the above type which is small, light-weight, and highly portable for use in remote field locations.

Toward the fulfillment of these and other objects, according to the calorimeter and method of the present invention, a fixed volume of gas is burned in a controlled environment and the temperature changes of the air in the environment caused by the burning is measured. The calorific value of the gas is determined based on the temperature measurement.

BRIEF DESCRIPTION OF THE DRAWINGS

The above brief description, as well as further objects, features and advantages of the present invention will be more fully appreciated by reference to the following detailed description of the presently preferred but nonetheless illustrative embodiment in accordance with the present invention when taken in conjunction with the accompanying drawings in which.

DESCRIPTION OF THE PREFERRED EMBODIMENT

Figure 1:
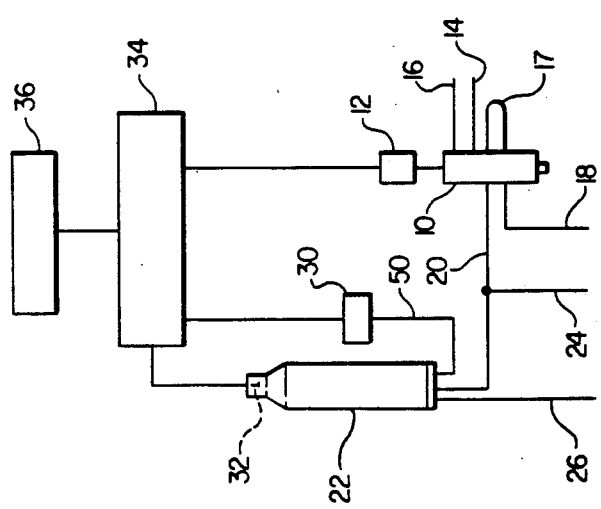
FIG. 1 is a schematic view depicting the calorimeter of the present invention.

Referring specifically to FIG. 1 of the drawings, the reference numeral 10 refers in general to a gas sampling valve which is driven by a solenoid 12 between two positions as will be described. The valve 10 has two inlets for respectively receiving gas and air from tubes 14 and 16 which are connected to sources of gas and air, respectively. A U-shaped sample tube 17 registers with two ports of the valve 10 for reasons to be described, and two outlets are formed in the valve 10 and are respectively connected to outlet tubes 18 and 20. The outlet tube 18 is vented to atmosphere and the outlet tube 20 is connected to an inlet of a burner assembly 22. An air tube 24 is connected to the tube 20 for introducing additional air into the burner assembly 22 as will be described, and a sweep air tube 26 is connected directly into another inlet formed in the burner assembly 22.

A transformer 30 is electrically connected to the burner assembly 22 for supplying high voltage, low current electricity to the burner assembly 22 for igniting the combustible gas with an electrical spark, as also will be described. A temperature sensing device 32, which may be in the form of a thermister or the like, is disposed in the upper end of the burner assembly 22 and is electrically connected to a microprocessor 34 which processes the signal and provides various outputs. A display 36 is connected to the microprocessor for displaying the results of the measurements in a conventional manner.

Figure 2:
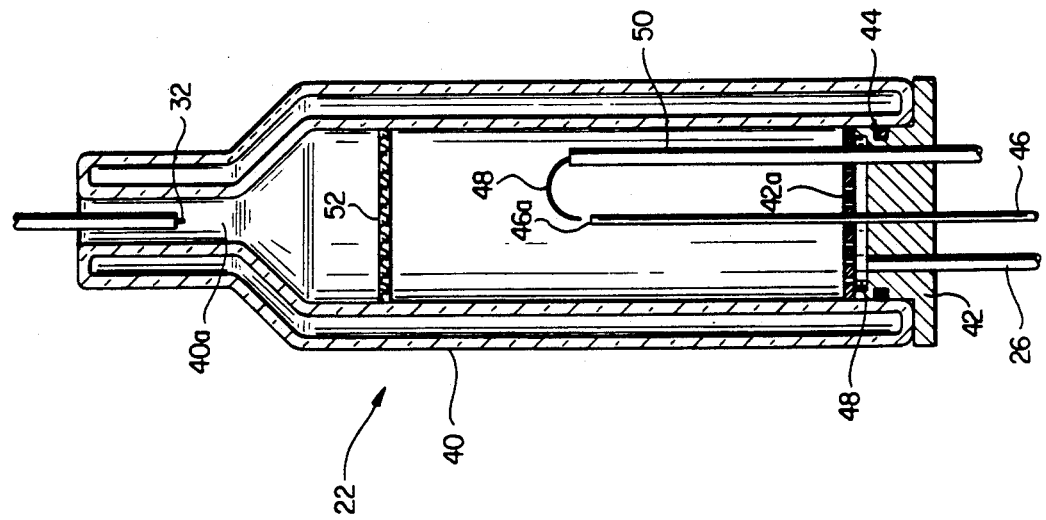
FIG. 2 is a front elevational view of the burner assembly of the calorimeter of FIG. 1.

The burner assembly 22 is shown in detail in FIG. 2 and includes a thermally insulated housing 40 which can be in the form of a glass, double-walled cylinder which contains a vacuum between the walls, with the surfaces adjacent to the evacuated portion being silvered in a conventional manner.

An outlet passage 40a is found in the upper end of the housing 40 as viewed in FIG. 1, and the open lower end of the housing is sealed with a base plate 42. An O-ring 44 extends around a notch formed in the outer surface of the base plate 42 and is in engagement with the inner wall of the housing 40. A burner tube 46 extends through the base plate 42 and into the interior of the housing 40, and is connected at the other end to the tube 20 (FIG. 1). Also penetrating the base plate 42 is an electrically insulated high-voltage wire 48 having insulation 50 extended throughout most of its length, but having its free and portion stripped of the insulation. The other end of the wire 48 is electrically connected to the transformer 30 as shown in FIG. 1. The free, uninsulated, end of the wire 48 is in close proximity to the tip 46a of the burner tube 46 to permit an electrical spark to travel from the wire to the tip, or to a ground wire in close proximity to the tip.

The air tube 26 penetrates the base plate 42 and registers with a cavity 49 formed in the base plate to supply air to the cavity. The upper surface 42a of the base plate contains a series of openings which distribute the air supplied by the tube 26 into the interior of the housing 40. The air flows upwardly and discharges through the outlet passage 40a to provide a uniform or otherwise controlled air flow through the housing 40 to remove heat from the interior of the housing. Further details regarding the base plate 42 and control of air flow using that plate 42 are depicted in or may be better understood with reference to FIGS. 3-5.

Figure 3:
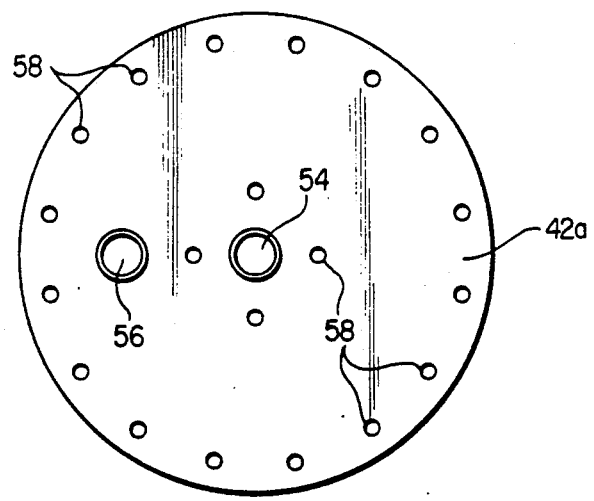
FIG. 3 is a top plan view of a base plate that can be incorporated into embodiments of the present invention.
Figure 4:
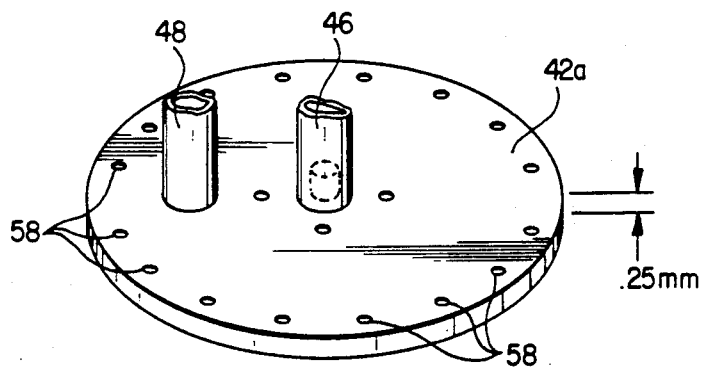
FIG. 4 is a front elevational view of the base plate shown in FIG. 3.

Referring to FIG. 3, shown therein is the top surface 42a of a base plate 42 that can be incorporated into embodiments of the present invention. The base plate 42 may be seen to have two large holes 54, 56 through it, through which gas line 46 and high voltage line 48, respectively, may pass. Additionally, the base plate 42 may be seen to have a plurality of other holes 58. These holes or perforations or openings (as previously discussed) operate to distribute the air supplied by the tube 26 into the interior of the housing 40. Needless to say, the holes 58 can be configured in any of a large number of patterns. One such pattern could comprise uniformly spaced holes to cause uniform distribution of air flow. Another pattern, such as is shown in FIG. 3, could involve more perforations positioned around the outside diameter of the plate 42 than positioned towards the center of the plate 42. It has been found in actual tests that such a pattern provides substantially increased air flow along the inside walls of the housing, resulting in faster heat transfer back to the air and reduced heat loss in the walls. Thus, a shorter cycle time can be achieved. By way of example only, plate thickness in a plate such as shown in FIG. 3 could be on the order of 0.25 mm these could be some twenty holes through the plate, of which about sixteen are evenly spaced around the periphery thereof and each having a diameter of about 0.36 mm. FIG. 4 is a front elevational view of the plate 42 of FIG. 3 showing lines 46 and 48 passing up through that plate 42.

Figure 5:
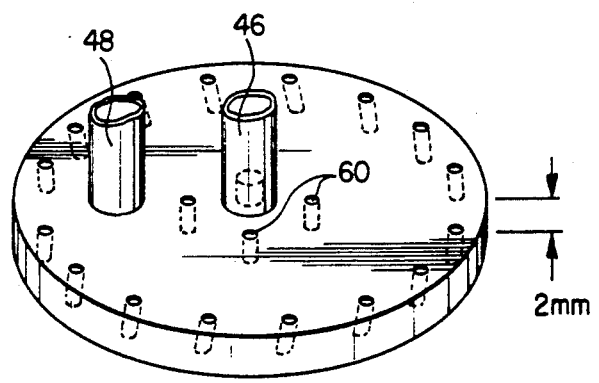
FIG. 5 is a front elevational view, partially schematic, of an alternative base plate that can be incorporated into embodiments of the present invention.

Referring now to FIG. 5, an alternative base plate 42 is shown therein. This alternative base plate is thicker than the one discussed above (e.g., 2 mm rather than 0.25 mm) and has slanted holes therethrough (e.g., at a 45° angle). This type of configuration has been found to produce a directed air stream that rotates or swirls inside the housing against the inside walls. This increases the path length of the air flowing along the wall and further improves heat transfer to the air. Some other holes 60, also slanted, can be drilled or otherwise formed on the inside area of the plate 42. These holes can be "aimed" at the burner tube to minimize backwards heat loss by conduction along the tube. Again, this reduces the time cycle for each measurement.

Referring now back to FIG. 2, a heat sink 52 is disposed within the interior of the housing 40 above the burner tip 46a and can be in the form of a copper or brass screen.

The gas sampling valve 10 operates in a conventional manner between two positions as determined by the position of the solenoid 12. In the first position, a gas flows from the inlet tube 14, enters the valve 10, and flows through the valve and the sample tube 17 before returning back into the valve and flowing out again through the vented outlet tube 18. When the supply of gas from the source is cut off, gas will thus accumulate in the tube 17. Also in this first position of the valve 10, air enters the valve through the inlet tube 16 and discharges from the valve into the outlet tube 20.

In the second position of the valve 10, the supply of sample gas is either cut off or routed directly from the inlet tube 14 to the vented outlet tube 18. The air entering through the tube 16 is routed through the sample tube 17 and then to the burner supply tube 20. During this flow, the gas that accumulated in the sample tube 17 in the previous position of the valve 10 will be forced into the outlet tube 20 by, and along with, the air. Thus, the volume of gas introduced from the tube 20 into the burner assembly 22 is precisely known since it corresponds to the capacity of the sample tube 17.

The operation, the microprocessor 34 responds to signals from the heat sensor 32 and makes temperature measurements of the air in the passage 40a of the housing 40 immediately below the heat sensor 32, at a constant rate and at a predetermined amount of times per second. These readings, or their sum, is stored in the memory of the microprocessor 34 and, after a few seconds, the sample valve 10 is energized as described above to permit a fixed volume of the combustible gas to flow from the valve, through the outlet tube 20 and into the burner tube 46, along with a constant flow of constant temperature air from the valve and the primary air tube 24. Also, additional air is distributed through the housing 40 from the air tube 26 through the openings in the upper surface 42a of the base plate 42.

The transformer 30 is energized just prior to the arrival of the combustion gas at the burner tube tip 46a to cause a spark to emit from the wire 48 and ignite the gas sample. The transformer 30 is turned off and the entire gas sample burns around the burner tube tip 46a to heat the air in the housing immediately below the heat sensor 32 and thus raise its temperature to a maximum value. After a period of time after the gas is completely burned, the temperature of the air just below the heat sensor 32 will begin decreasing from the maximum value. The microprocessor 34 continues reading the temperature of the air until the temperature returns to that of the starting temperature at which time the microprocessor completes processing the temperature data and displays the result on the display 36.

The heat sink 52 lowers the peak temperature reached by the exit air, thus permitting the heat sensor 32 to measure the rapidly changing temperature more accurately. Also, the heat sink 52 retains, for a short time, a large portion of the heat released by the flame, thus delaying the heat release until the mixture of air and combustion products has left the interior of the housing 40. This improves the accuracy of the measurements by reducing any error caused by differences in heat capacities of air in an air combustion product mixture.

In practice, several sample burns are made to bring the exit air temperature to about 10°-20° F. above that of the supply air temperature. When this is done, and the cool-down rate of the exit air becomes about 0.5° F. per minute, repeat measurements can be made at a faster rate, i.e., at about one measurement per minute.

The microprocessor 34 determines the heat released by combustion of the gas sample by summing the differences in temperature between a base temperature measured just prior to the ignition of the sample and each temperature measured over the period of time required to return to the starting temperature. This summation, of course, is a functiona of the quantity of heat released by combustion of the gas sample, and the calorific value of the latter can then be obtained by comparison with a scale or data based on identical measurements of gases of known calorific value.

It should be noted that the highest temperature measured by the heat sensor 32 in the period of the required for the air to return to the starting temperature, or other fixed temperature, are also functions of the calorific value of the gas sample and therefore these parameters can also be used to measure the calorific value.

It is thus seen that the present invention enables an accurate calorific value of the gas sample to be measured utilizing a relative low volume (as low as one milliliter) of gas. Also, since the temperature of the air surrounding the burning sample is immediately reduced after attaining a peak value, heat losses are minimized, tus eliminating the necessity of expensive gas and air metering components and environmental control systems. Also, it is understood that the foregoing components of the calorimeter of the present invention can be housed in a relatively small package and is thus small, lightweight, and highly portable for use in remote field locations.

Other modifications, changes and substitutions are intended in the foregoing disclosure and, in some instances, some features of the invention can be employed without a corresponding use of other features. Accordingly, it is appropriate that the appended claims be construed broadly and in a manner consistent with the scope of the invention therein.

What is claimed is:

1. A gas calorimeter comprising:
    means for intermittently supplying a small, fixed volume of gas to a controlled environment including a heat sink disposed therein,
    means for burning said gas in said environment to increase the temperature of air in said environment and the heat sink, and
    means for measuring the changes in the temperature of said heated air to enable the calorific value of said gas to be determined.
    wherein said controlled environment comprises a thermally insulated housing having portions defining at least one opening therethrough, and
    wherein said means for intermittently supplying comprises a base plate with a periphery and a center, said base plate peripherally sealed over said at least one opening in said thermally insulated housing, said base plate having portions defining a plurality of dispersion holes therethrough in a distributed manner so that a greater number of said plurality of dispersion holes are in and around the periphery of said base plate than are in and toward the center of said base plate.

2. A gas calorimeter as recited in claim 1 wherein said base plate has an upper surface and a lower surface, wherein each of said plurality of dispersion holes has a generally cylindrical wall so as to thereby have a central axis, and wherein at least some of said plurality of dispersion holes pass through said base plate with their central axis not orthogonal relative to either said upper or said lower surface of said base plate.

3. A gas calorimeter as recited in claim 2, wherein said base plate is about 2 mm thick between its upper and lower surfaces, and wherein said base plate has about twenty dispersion holes therethrough of which about sixteen are evenly spaced around the periphery thereof, said sixteen evenly spaced dispersion holes passing through said base plate with their central axis defining angles of about forty-five degrees with said upper and said lower surfaces of said base plate.

4. A gas calorimeter as recited in claim 1, wherein said base plate has an upper and a lower surface and is about 0.25 mm thick therebetween, and wherein said base plate has about twenty dispersion holes therethrough of which about sixteen are evenly spaced around the periphery thereof.

5. A gas calorimeter in claim 1, wherein said means for burning comprises a burner tube at least partially disposed within said thermally insulated housing, and wherein said plurality of dispersion holes in the generally central portion of said base plate are slanted so as to effectively aim gas passing therethrough at said burner tube.

6. A method of measuring the calorific value of a gas comprising the steps of:
    intermittently supplying a small, fixed volume of said gas to a controlled environment including a heat sink disposed therein,
    burning said gas in said environment to increase the temperature of the gas and the heat sink, and
    measuring the changes in the temperature of said heated air to enable the calorific value of said gas to be determined wherein said method is capable of measuring gross calorific and
    wherein said controlled environment comprises a thermally insulated housing having portions defining at least one opening therethrough, and
    wherein said step of intermittently supplying comprises the step of passing said gas through a base plate with a periphery and a center, said base plate periphery sealed over said at least one opening in said thermally insulated housing, said base plate having portions defining a plurality of gas dispersion holes therethrough in a distributed manner so that a greater number of said plurality of dispersion holes are in and around the periphery of said base plate than are in and toward the center of said base plate.

7. A method as recited in claim 6, wherein said base plate has an upper surface and a lower surface, wherein each of said plurality of dispersion holes has a generally cylindrical wall so as to thereby have a central axis, and wherein at least some of said plurality of dispersion holes pass through said base plate with their central axis not orthogonal relative to either said upper or said lower surface of said base plate.

8. A method as recited in claim 7, wherein said base plate is about 2 mm thick between its upper and lower surfaces, and wherein said base plate has about twenty dispersion holes therethrough of which about sixteen are evenly spaced around the periphery thereof, said sixteen evenly spaced dispersion holes passing through said base plate with their central axis defining angles of about forty-five degrees with said upper and lower surfaces of said base plate.

9. A method as recited in claim 6, wherein said base plate has an upper and a lower surface and is about 0.25 mm thick therebetween, and wherein said base plate has about twenty dispersion holes therethrough of which about sixteen are evenly spaced around the periphery thereof.

10. A method as recited in claim 6, wherein said means for burning comprises a burner tube at least partially disposed within said thermally insulated housing and wherein said plurality of dispersion hole in the generally central portion of said base plate are slanted so as to effectively aim gas passing therethrough at said burner tube.

11. A gas calorimeter comprising:
means for discharging a small fixed volume of gas to be measured to a controlled environment including a heat sink disposed therein and for terminating said discharging after said gas has entered said environment,
means for burning said gas in said environment, and
means for measuring the changes in the temperature of said heated air,
whereby the changes in temperature of said heated air in said environment enables the calorific value of said gas to be determined,
wherein said controlled environment comprises a thermally insulated housing having portions defining at least one opening therethrough, and
wherein said means for intermittently supplying comprises a base plate with a periphery and a center, said base plate peripherally sealed over said at least one opening in said thermally insulated housing, said base plate having portions defining a plurality of dispersion holes therethrough in a distributed manner so that a greater number of said plurality of dispersion holes are in and around the periphery of said base plate than are in and toward the center of said base plate.

12. A gas calorimeter as recited in claim 11 wherein said base plate has an upper surface and a lower surface, wherein each of said plurality of dispersion holes has a generally cylindrical wall so as to thereby have a central axis, and wherein at least some of said plurality of dispersion holes pass through said base plate with their central axis not orthogonal relative to either said upper or said lower surface or said base plate.

13. A gas calorimeter as recited in claim 12, wherein said base plate is about 2 mm thick between its upper and lower surfaces, and wherein said base plate has about twenty dispersion holes therethrough of which about sixteen are evenly spaced around the periphery thereof, said sixteen evenly spaced dispersion holes passing through said base plate with their central axis defining angles of about forty-five degrees with said upper and said lower surfaces of said base plate.

14. A gas calorimeter as recited in claim 11, wherein said base plate has an upper and a lower surface and is about 0.25 mm thick therebetween, and wherein said base plate has about twenty dispersion holes therethrough of which about sixteen are evenly spaced around the periphery thereof.

15. A gas calorimeter in claim 11, wherein said means for burning comprises a burner tube at least partially disposed within said thermally insulated housing, and wherein said plurality of dispersion holes in the generally central portion of said base plate are slanted so as to effectively aim gas passing therethrough at said burner tube.

16. A method of measuring the calorific value of a gas comprising the steps of discharging a small, fixed volume of gas to a controlled environment including a heat sink disposed therein,
terminating said step of discharging after said gas has entered said environment,
burning said gas in said environment to heat the air in said environment, and
measuring the changes in the temperature of said heated air,
whereby the changes in the temperature of said heated air in said environment enables the calorific value of said gas to be determined,
wherein said controlled environment comprises a thermally insulated housing having portions defining at least one opening therethrough, and
wherein said step of intermittently supplying comprises the step of passing said gas through a base plate with a periphery and a center, said base plate periphery sealed over said at least one opening in said thermally insulated housing, said base plate having portions defining a plurality of gas dispersion holes therethrough in a distributed manner so that a greater number of said plurality of dispersion holes are in and around the periphery of said base plate than are in and toward the center of said base plate.

17. A method as recited in claim 16, wherein said base plate has an upper surface and a lower surface, wherein each of said plurality of dispersion holes has a generally cylindrical wall so as to thereby have a central axis, and wherein at least some of said plurality of dispersion holes pass through said base plate with their central axis not orthogonal relative to either said upper or said lower surface of said base plate.

18. A method as recited in claim 17, wherein said base plate is about 2 mm thick between its upper and lower surfaces, and wherein said base plate has about twenty dispersion holes therethrough of which about sixteen are evenly spaced around the periphery thereof, said sixteen evenly spaced dispersion holes passing through said base plate with their central axis defining angles of about forty-five degrees with said upper and lower surfaces of said base plate.

19. A method as recited in claim 16, wherein said base plate has an upper and a lower surface and is about 0.25 mm thick therebetween, and wherein said base plate has about twenty dispersion holes therethrough of which about sixteen are evenly spaced around the periphery thereof.

20. A method as recited in claim 16, wherein said means for burning comprises a burner tube at least partially disposed within said thermally insulated housing and wherein said plurality of dispersion hole in the generally central portion of said base plate are slanted so as to effectively aim gas passing therethrough at said burner tube.

* * * * *

UNITED STATES PATENT AND TRADEMARK OFFICE
CERTIFICATE OF CORRECTION

PATENT NO. : 5,100,244
DATED : March 31, 1992
INVENTOR(S) : Duane V. Kniebes

It is certified that error appears in the above-identified patent and that said Letters Patent is hereby corrected as shown below:

Col. 3, Line 12

Delete (49) and insert 48

Col. 5, Line 27

Delete (tus) and insert thus

Signed and Sealed this

Twenty-third Day of November, 1993

Attest:

BRUCE LEHMAN

*Attesting Officer*     *Commissioner of Patents and Trademarks*